(12) United States Patent
Xinsheng et al.

(10) Patent No.: US 8,196,575 B2
(45) Date of Patent: Jun. 12, 2012

(54) METHOD AND AN APPARATUS FOR MONITORING AND CONTROLLING FLOWS

(75) Inventors: Li Xinsheng, Shenzhen (CN); Zhou Xiaoyong, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 1379 days.

(21) Appl. No.: 11/636,082

(22) Filed: Dec. 8, 2006

(65) Prior Publication Data

US 2007/0163579 A1 Jul. 19, 2007

(30) Foreign Application Priority Data

Jan. 13, 2006 (CN) .......................... 2006 1 032990

(51) Int. Cl.
*A61M 15/00* (2006.01)
(52) U.S. Cl. ............................. 128/203.14; 128/203.12
(58) Field of Classification Search ............. 128/200.24, 128/203.12–203.14, 203.28–203.29, 204.18–204.21, 128/204.23, 204.26, 204.28, 205.13–205.14, 128/205.24–205.25, 207.14–207.29
See application file for complete search history.

(56) References Cited

U.S. PATENT DOCUMENTS

| | | | | |
|---|---|---|---|---|
| 4,747,403 A | * | 5/1988 | Gluck et al. | 128/204.21 |
| 5,165,397 A | * | 11/1992 | Arp | 128/204.21 |
| 5,438,980 A | | 8/1995 | Phillips | |
| 5,598,838 A | | 2/1997 | Servidio | |
| 6,119,686 A | * | 9/2000 | Somerson et al. | 128/202.22 |
| 6,371,113 B1 | * | 4/2002 | Tobia et al. | 128/204.23 |
| 7,128,578 B2 | * | 10/2006 | Lampotang et al. | 434/365 |
| 2005/0061321 A1 | * | 3/2005 | Jones | 128/204.18 |
| 2005/0076906 A1 | * | 4/2005 | Johnson | 128/204.21 |
| 2005/0087190 A1 | * | 4/2005 | Jafari et al. | 128/204.21 |

FOREIGN PATENT DOCUMENTS

| | | |
|---|---|---|
| CN | 2102092 U | 4/1992 |
| CN | 2628073 Y | 4/2004 |
| DE | 102004014619 A | 3/2005 |
| WO | 2006067822 A1 | 6/2006 |

* cited by examiner

*Primary Examiner* — Justine Yu
*Assistant Examiner* — Rachel Young
(74) *Attorney, Agent, or Firm* — Kerry D. Christensen; Stoel Rives LLP

(57) ABSTRACT

A method and an apparatus for monitoring and controlling flows in medical equipment including an anesthetic machine and a ventilator for influencing a patient's respiratory system are disclosed. The apparatus includes a microprocessor and an airway system including drive gas conduits provided with an inhalation valve (2) and an exhalation valve (5) for gas discharging as well as a ventilator end flow sensor (3) for measuring the introduced or discharged drive gas flow through the valves. The airway system also includes patient end breathing tubing in which a patient end flow sensor (11) for measuring the patient's inspired and expired gas flow is provided. By comparing the measured values of the two flow sensors against the characteristic curve of the inhalation valve (2), the microprocessor can judge the operation states and accuracy of the respective flow sensors and the inhalation valve (2).

12 Claims, 2 Drawing Sheets

METHOD AND AN APPARATUS FOR MONITORING AND CONTROLLING FLOWS

STATEMENT OF RELATED APPLICATION

The present application claims the priority of the Chinese Patent Application No. 200610032990.2, filed on Jan. 13, 2006, entitled "A Method and an Apparatus for Monitoring and Controlling Flows", which is incorporated herein by reference in its entirety.

FIELD OF THE INVENTION

The present invention relates to medical equipment, and more particularly to a method and an apparatus for monitoring and controlling flows in medical equipment that influence a patient's respiratory system by processing the gas.

BACKGROUND OF THE INVENTION

An anesthetic machine is auxiliary equipment for guiding a patient to inhale anesthetic gas and for mechanical ventilation during an operation. Flow and airway pressure are the most basic parameters which the anesthetic machine monitors, and the calculation of other parameters or even the whole mechanical ventilation process control is based thereon. Therefore, the precision and stability in measuring and testing these two parameters determines not only the accuracy and safety of the anesthetic machine in controlling the mechanical ventilation but also the ventilation modes that the anesthetic machine adopts and the performance that the anesthetic machine can achieve. The present invention is related mainly to the monitoring and controlling of the flow, the more important and also more difficult parameter to be accurately monitored.

Depending on the locations where the measurements are made, prior art methods for monitoring flows in the anesthetic machine are classified as the patient end monitoring and the anesthetic machine end monitoring.

The patient end monitoring is also referred to as the proximal end monitoring, wherein the flow monitoring point is located close to the respiratory tract of the patient. This type of monitoring has found very wide application in the currently available products, which is mainly executed in the following two forms: 1) a flow sensor is installed downstream of the Y-shaped connector in the patient breathing circuit for simultaneously monitoring the velocity of the exhaled and inhaled gas; 2) two flow sensors are installed in the exhaling conduit and the inhaling conduit of the patient breathing circuit respectively for separately monitoring the velocity of the exhaled and inhaled gas. These two forms are all directed to the measurement of the flow velocity in the patient breathing circuit. Since the measuring point is located near the respiratory tract of the patient, the influence of the leakage from conduits and the change of compliance on the measurement can be reduced remarkably, so that the measured value is substantially equal to the gas flow that is delivered actually into the patient's lungs. High measuring accuracy and sensitivity are thereby ensured. However, the same fact that the measuring point is located near the respiratory tract of the patient also produces unfavorable effect, because in this case the flow sensor is affected easily by the secretions of the respiratory tract of the patient and the water vapor condensate in the respiratory conduit such that the measured results may deviate from the true values and that the ventilation control may be disabled.

The anesthetic machine end monitoring is also referred to as the distal end monitoring, wherein the flow monitoring point is located inside the anesthetic machine and far away from the respiratory tract of the patient. The flow sensor is usually installed following the inhalation valve inside the anesthetic machine for monitoring the flow of the drive gas flowing out of the inhalation valve. The flow of the drive gas within one breathing cycle is regarded as equal to the tidal volume inhaled by the patient. Since the drive gas flowing through the flow sensor is dry, the measured value is free from the influence of the water vapor condensate and the secretions in the patient breathing circuit. However, since it is the flow of the drive gas that is measured, which is influenced by the leakage from conduits and the change of compliance, this measured flow deviates from the actual ventilation volume in certain degree. Moreover, this deviation can not be compensated because the amount of the leakage and the extent of the change of compliance in the breathing circuit can not be monitored. In addition, with respect to the realization of some respiratory functions, flow speed trigger and the like can not be realized because the flow sensor is located far away from the patient end. As a result, the distal end monitoring is vanishing from the market.

The closed-loop flow control means to control the opening of the inhalation valve by using the measured value of the flow sensor as the feedback signals and thus control the ventilation volume for the patient. Specifically, the measured value of the flow sensor is compared with a preset value, and if the two values are inconsistent, the microprocessor will adjust the opening of the inhalation valve according to the deviation between the two values until the two values reach consistency. Regardless of a patient end flow monitoring or an anesthetic ventilator end flow monitoring, this control mode has a serious defect. When the measured value of the flow sensor largely deviates from the preset value, there is no way to determine the causes for the deviation, for example, whether it is caused by the inaccurate measurements of the flow sensor or resulted from changes in the characteristics of the inhalation valve. To make the parameters concerning the flow monitoring consistent with the preset parameters, it is generally only possible to adjust the inhalation valve against the measured value of the sensor. In this way, the user is unable to find out the deviation in the sensor measurements. As a further result, the actual ventilation volume supplied to the patient is not consistent with the predetermined volume and so it is not possible to ensure the safety of the mechanical ventilation. In order to ensure the patient's safety, a common prior solution is to use the characteristic curve of the inhalation valve as the basis for the judgment. When the deviation between the ventilation volume derived from the characteristic curve and the value measured with the flow sensor exceeds the predetermined threshold value, but at the same time the monitored result of the inhalation valve control circuit shows that the inhalation valve works normally, the anesthetic machine will judge immediately that a sensor failure has occurred and will suspend the flow monitoring. Where the anesthetic machine continues its operation, it can only depend on the inhalation valve itself to control the flow. As such, due to lack of flow monitoring, the influence of the inhalation valve on the ventilation volume arisen from the control circuit drift and the change in the own characteristics as well as the leakage from conduits and the compliance is unable to be eliminated. As a result, a rather serious deviation between the actual ventilation volume and the predetermined value may still exist. Therefore, the accuracy and safety in using an anesthetic machine to apply mechanical ventilation to the patient can still hardly be guaranteed.

To sum up, the prior technology for monitoring and controlling the flow in an anesthetic machine is subjected to the following disadvantages:

1. The distal end monitoring can not guarantee that the monitored ventilation volume corresponds to the patient's actual inhaling volume, and moreover, it can not realize flow trigger; on the other hand, though the proximal end monitoring achieves relatively high precision and sensitivity, it often gives rise to greater measurement deviation and even causes the measurements to be invalidated when the flow sensor is exposed to heavy water vapor condensation within the respiratory conduit in the course of use.

2. By using single proximal end or distal end flow measurement method, when deviation or invalidation appears in the flow sensor or in the inhalation valve, the system can only adjust one against the other. This kind of treatment mechanism can not guarantee the accuracy of the ventilation control. Moreover, the safety of the mechanical ventilation can not be guaranteed when great deviations occur to the benchmark, and it is even possible to cause injuries to the patient.

The above-mentioned problems also exist in other medical equipment including ventilators which are used to influence a patient's respiratory system. Among them, the safety problem of an anesthetic machine is particularly concerned.

SUMMARY OF THE INVENTION

In view of the above described deficiencies of the prior art, it is an object of the present invention to provide an improved method and apparatus for monitoring and controlling flows in medical equipment including anesthetic machines and ventilators which are used to influence a patient's respiratory system, in order to realize accurate flow monitoring and controlling, and in turn to guarantee the accuracy and safety in controlling the mechanical ventilation.

The essence of the present invention is that a flow sensor is respectively installed both inside the anesthetic machine or the ventilator and in the breathing circuit at the patient end so as to monitor the flow of the inhaled and exhaled gas by the patient at both the distal end and the proximal end simultaneously, and that by comparison of the measured values of two flow sensors against the characteristic curve of the inhalation valve, the microprocessor is capable of detecting the working states and accuracy of each sensor and the inhalation valve. Thus, the accuracy of the flow monitoring and the safety of the ventilation control in anesthetic machines or ventilators are guaranteed.

According to an aspect of the present invention, there is provided an apparatus for monitoring and controlling flows in medical equipment including an anesthetic machine and a ventilator for influencing a patient's respiratory system. This apparatus comprises a power supply, a microprocessor, an airway system, several microprocessor-controlled valve state monitoring units and valve actuating units and sensor data collecting and receiving units. The airway system comprises a bellows, drive gas conduits at a ventilator end and breathing tubing at a patient end connected respectively to an outer chamber and a gasbag of the bellows. The drive gas conduits are provided with an inhalation valve and an exhalation valve for gas discharging, and the breathing tubing at the patient end comprises an inhaling conduit and an exhaling conduit. The inhalation valve is connected to corresponding valve state monitoring units and valve actuating units. Besides, this apparatus further comprises a ventilator end flow sensor provided in the drive gas conduits and a patient end flow sensor in the breathing tubing, wherein output signals from the ventilator end flow sensor and the patient end flow sensor are delivered to the respective sensor data collecting and receiving units.

In the above described apparatus, the patient end flow sensor is either a two-way flow sensor installed following a Y-shape connector which connects the patient end breathing tubing to the patient, or is replaced with two one-way flow sensors respectively installed in the inhaling conduit and the exhaling conduit, used for measuring inhaled and exhaled gas flows of the patient.

In the above-described apparatus, the ventilator end flow sensor is either a two-way or a one-way flow sensor installed in the drive gas conduit connecting the inhalation valve with the bellows.

According to another aspect of the present invention, there is provided a method for monitoring and controlling flows adapted for use in medical equipment including an anesthetic machine and a ventilator for influencing a patient's respiratory system, which equipment comprises a microprocessor, an airway system, several microprocessor-controlled valve state monitoring units and valve actuating units as well as sensor data collecting and receiving units. The airway system comprises drive gas conduits connecting an inhalation valve and an exhalation valve for gas-discharging as well as an equipment end flow sensor for measuring the drive gas flow introduced or discharged through the inhalation valve. The airway system further comprises a patient end breathing tubing provided with a patient end flow sensor for measuring inhaled or exhaled gas flow of the patient. This method comprises the following steps:

A. the microprocessor actuates the airway system into an inhaling control period and an exhaling control period alternately through the valve actuating units;

B. the microprocessor monitors control parameters of the inhalation valve through the valve state monitoring units;

C. the microprocessor acquires gas flow values monitored and measured by the equipment end flow sensor and the patient end flow sensor through the sensor data collecting and receiving units;

D. the microprocessor analyzes and compares the control parameters with the respective measured gas flow values during the same inhaling control period or exhaling control period, and conducting adjustment based on the analyzed and compared result.

In the above-described method, the control parameters comprise the gas flow the inhalation valve actually inhales during the inhaling control period, which is the integration of the gas delivering velocity and the gas delivering time through the inhalation valve.

In the above-described method, safety threshold values are correspondingly determined to limit the deviations between the control parameters and the respective measured gas flow values and between the respective measured gas flow values themselves. These safety threshold values are applied in the analysis and comparison in step D.

The above-described technical solutions according to the present invention make it possible to maintain both the advantage of a patient end flow monitoring and that of a ventilator end flow monitoring. That is to say, it not only assures of excellent monitoring sensitivity and accuracy, but also resist the influence of damp and water condensation and stabilize the monitoring result, so as to realize the automatic and accurate compensation of ventilation volume. In addition, by comparing the values output from the two flow sensors and also with the control value of the inhalation valve, drifts or malfunctions occurring to the apparatus are able to be accurately determined. Of greater importance is that even either one of those two flow sensors is exposed to malfunction or valve drift, the flow remains in proper control. Thus, the safety and reliability of the apparatus are significantly improved, and this apparatus is of greater merits for clinical use due to no injuries to the patients.

BRIEF DESCRIPTION THE DRAWINGS

DESCRIPTION OF THE PREFERRED EMBODIMENTS

The present invention will be described hereunder in further details with reference to the preferred embodiments shown in the accompanying drawings.

Figure 1:
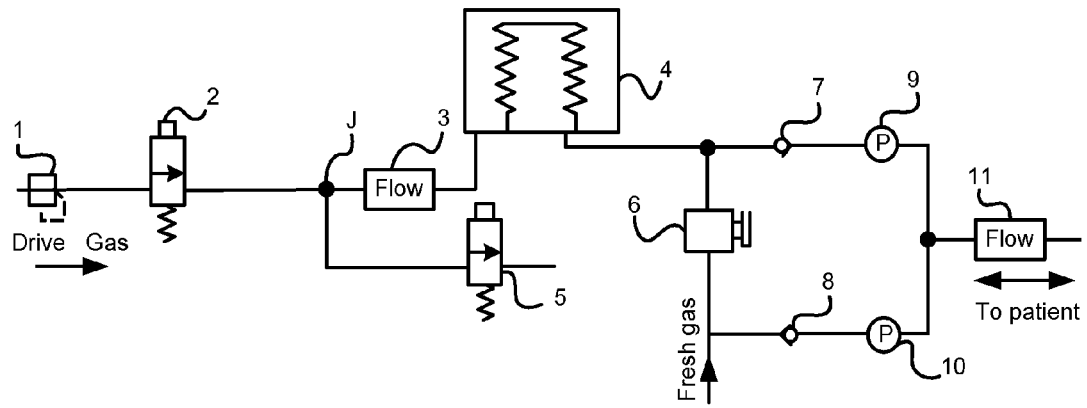
FIG. 1 is a schematic diagram illustrating the principle of the airway of an apparatus for monitoring and controlling flows according to the present invention.
Figure 2:
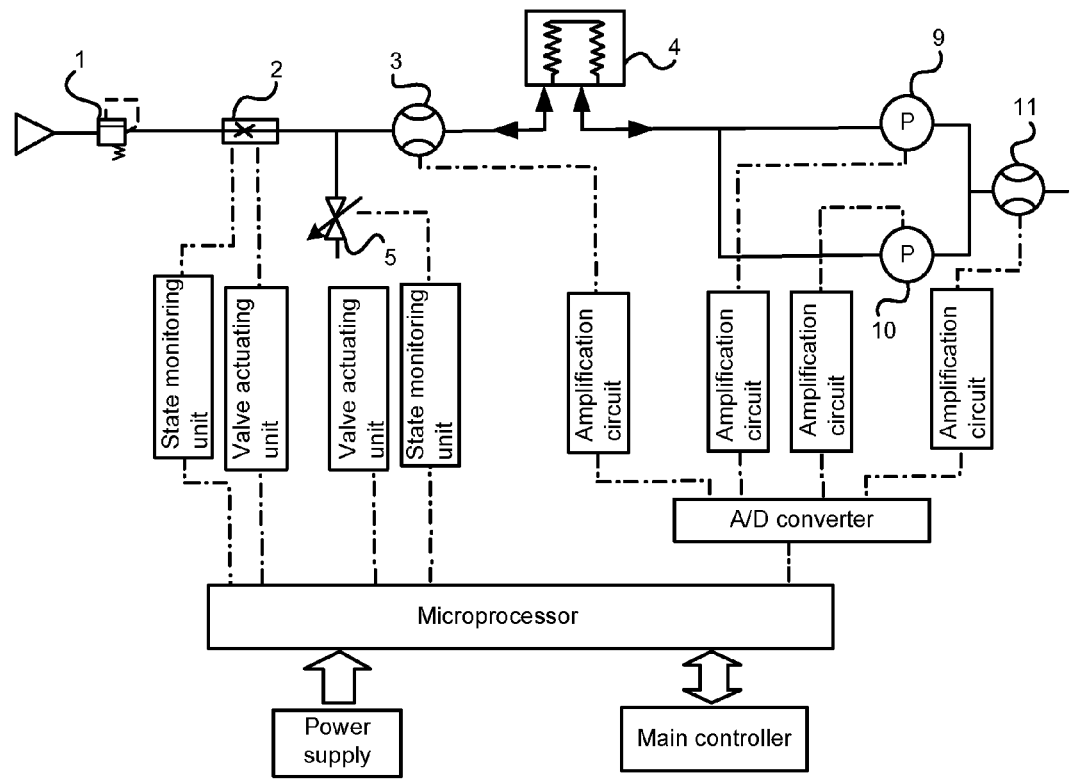
FIG. 2 is a system block diagram of an apparatus for monitoring and controlling flows according to the present invention.

As shown in FIG. 2, the apparatus for monitoring and controlling flows according to the present invention comprises a power supply, a microprocessor, an airway system, and several microprocessor-controlled valve state monitoring units, valve actuating units and data collecting and receiving units. The apparatus may further comprise microprocessor-controlled interface units for connecting a main controller (also known as a higher level controller). As shown in FIG. 1, the airway system comprises a bellows 4 and drive gas conduits at the ventilator end and breathing tubing at the patient end which are connected to the outer chamber and the gasbag of the bellows 4, respectively. The drive gas conduits connect a pressure-reducing valve 1, an inhalation valve 2 and an exhalation valve 5 which is used to vent the gas. The inhalation valve 2 and exhalation valve 5 are connected to the corresponding valve state monitoring units and valve actuating units, respectively, as shown in FIG. 2. Alternatively, it is also possible not to connect the exhalation valve 5 to the valve state monitoring unit. A ventilator end two-way flow sensor 3 is connected to the conduits between the junction J, where the inhalation valve 2 and exhalation valve 5 meet, and the bellows 4, for measuring both the flow of the drive gas introduced through the inhalation valve 2 and the flow of the drive gas discharged through the exhalation valve 5, respectively. The breathing tubing at the patient end comprises an inhaling conduit and an exhaling conduit. The inhaling conduit is provided with a carbon dioxide absorbent canister 6, an inhaling conduit check valve 8 and an inhaling conduit pressure sensor 10, and the exhaling conduit is provided with an exhaling conduit pressure sensor 9 and a check valve 7. In the case of an anesthetic machine, the inhaling conduit can also receive fresh gases including anesthetic gas from another gas delivering conduit. A patient end two-way flow sensor 11 can be integrated into the breathing tubing and is connected thereto following a Y-type connector which connects the patient end breathing tubing to the patient; alternatively, the patient end two-way flow sensor 11 can be replaced with two one-way flow sensors installed in the inhaling conduit and the exhaling conduit, respectively (not shown), for measuring the inhaled and exhaled gas flow. As shown in FIG. 2, the output signals of the ventilator end flow sensor 3 and the patient end flow sensor 11 are delivered respectively to the data collecting and receiving units which comprise a plurality of amplification circuits and A/D converters.

This is how the apparatus according to the present invention works. During the inhaling period, the exhalation valve 5 is controlled to be closed, while the inhalation valve 2 is controlled to be open and adjusted to a preset flow speed. The drive gas flows through the pressure reducing valve 1, the inhalation valve 2, then through the ventilator end flow sensor 3 and into the outer chamber of the bellows 4 and compresses there the gasbag inside the bellows downwards so that the gas inside the gasbag is forced to flow into the patient's lungs through the inhaling conduit and the patient end flow sensor 11 At that time, both the ventilator end flow sensor 3 and the patient end flow sensor 11 detect the positive inhaled gas flow. The gas flow values measured by the two flow sensors are substantially equal if fresh gas replenishment and the influence caused by the breathing tubing compliance are neglected, which is possible because the fresh gas flow introduced therein is usually only 2 to 5 L/min. The microprocessor calculates the inhaled amount of gas during the inhaling period based on the measurement of the flow sensor 3 or the flow sensor 11. When the inhaled amount of gas reaches the preset ventilation volume, it switches to the exhaling period, during which period the inhalation valve 2 is controlled to be closed, while the exhalation valve 5 is controlled to be open. Thereby, the gas flows from the patient end flow sensor 11 through the exhaling conduit back into the interior of the folded gasbag of the bellows 4, and pushes there the gasbag upwards to expel the drive gas from the outer chamber of the bellows 4 through the ventilator end flow sensor 3 and the exhalation valve 5. With the influence of the tubing compliance neglected, the gas flow values measured by the ventilator end flow sensor 3 and the patient end flow sensor 11 should be equal. Therefore, the gas volume actually exhaled during the exhaling period can be measured accurately by both the patient end flow sensor 11 and the ventilator end flow sensor 3.

The ventilator end flow sensor 3 provided in the apparatus for monitoring and controlling flows according to the present invention may simply be a flow sensor which only measures one-way flow velocity. In this case, the ventilator end flow sensor 3 can be alternatively connected between the inhalation valve 2 and the junction J, where the conduits of exhalation valve 5 and the bellows 4 meet (similar to the configuration of the two-way flow sensor as shown in FIG. 1). In this location, the ventilator end flow sensor 3 can be used to measure the flow of the introduced drive gas and be used as a benchmark to calibrate the patient end flow sensor 11 or the inhalation valve 2 when some devices are replaced with new ones or serious deviations occur to the measurements and controls.

As seen from above, the method for monitoring and controlling flows according to the present invention comprises the following steps:

A. the microprocessor actuates the airway system into an inhaling control period and an exhaling control period alternately through the valve actuating units;

B. the microprocessor monitors control parameters of the inhalation valve 2 through the valve state monitoring units;

C. the microprocessor acquires gas flow values monitored and measured by the equipment end flow sensor 3 and the patient end flow sensor 11 through the sensor data collecting and receiving units;

D. the microprocessor analyzes and compares the control parameters with the respective measured gas flow values during the same inhaling control period or the same exhaling control period, and carries out adjustment based on the analyzed and compared result.

The control parameters concerned comprise the gas flow the inhalation valve 2 actually inhales during the inhaling control period, which is the integration of the gas delivering velocity and the gas delivering time through the inhalation valve. During the inhaling period the control flow of the inhalation valve 2 and the measured flow of the equipment end flow sensor 3 should be equal theoretically under normal conditions, while the measured flow values of the patient end flow sensor 11 may slightly deviate from them due to the influence of tubing compliance and additional fresh gases. This deviation remains unchanged under the same breathing conditions. During the exhaling period, the exhaled gas flow value measured by the equipment end flow sensor 3 should be close to that by the patient end flow sensor 11 and have the same varying tendency. In the embodiments according to the present invention, depending on the difference in various ventilator airways and different requirements as to the accuracy in monitoring and controlling of the machines, corresponding safety threshold values are predetermined to confine the utmost deviations between these flow values. When the deviation exceeds the preset threshold value, the processor finds out the device(s) responsible for that deviation and makes corresponding adjustment or prompts the user.

Figure 3:
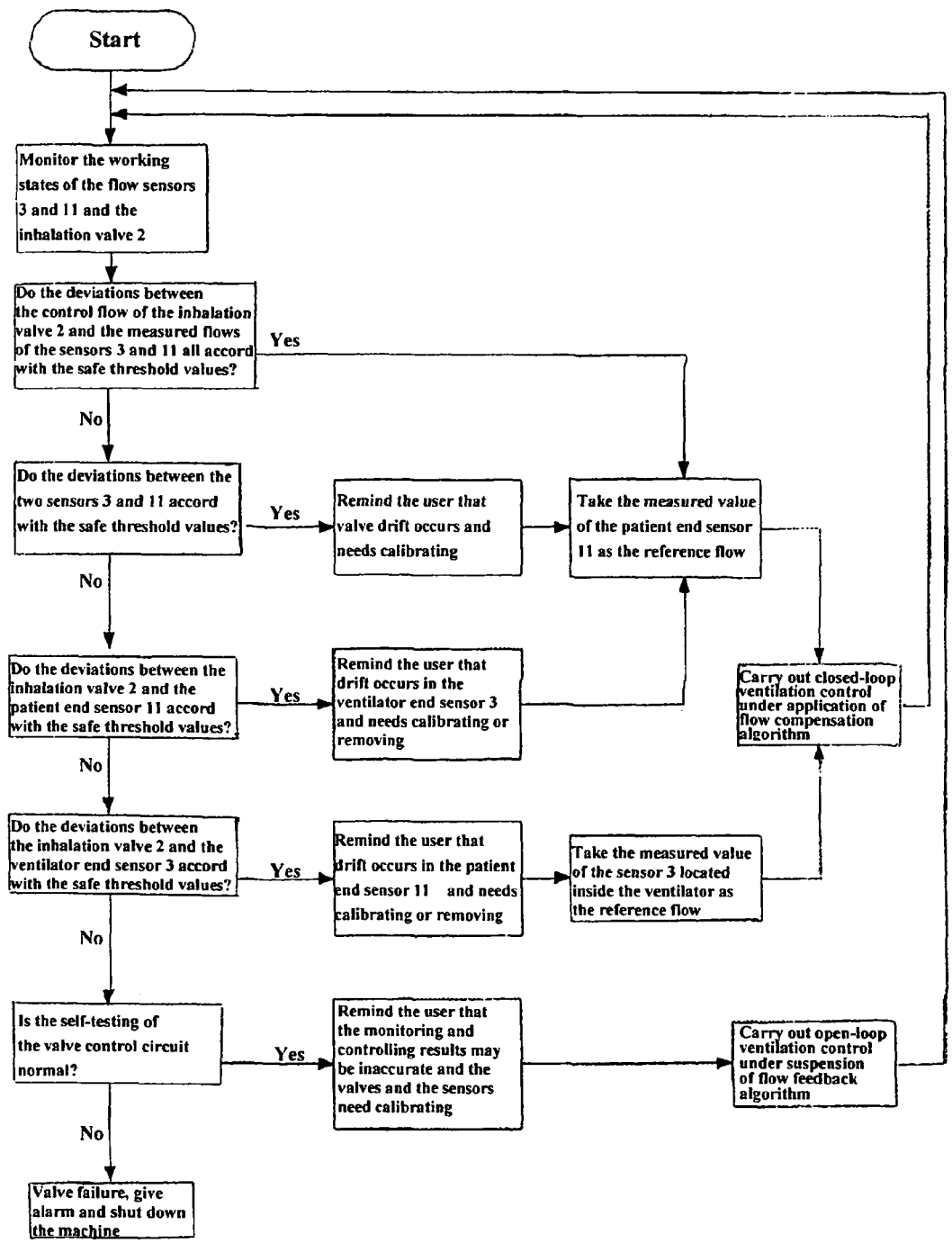
FIG. 3 is a flow chart of the process for monitoring and controlling flows according to the present invention.

FIG. 3 shows the flow diagram of the process for monitoring and controlling flows according to the present invention, illustrating the analyzing and controlling process as stated in step D of the above-described method, which is used mainly to judge whether the sensors and valves work normally during the operation. Specifically, the process needs to determine whether the deviations between the control flow of the inhalation valve 2, the measured flow of the ventilator end flow sensor 3 and the measured flow of the patient end flow sensor 11 are confined within the respective safety threshold values or not. If true, it indicates that the relevant devices work properly. The microprocessor then carries out a closed-loop flow control taking the measured value of the patient end flow sensor 11 as the reference value. In this way, it is possible to avoid the influence of the leakage from the conduits and the compliance on the ventilation volume, so as to ensure the accuracy and stability of the ventilation volume and correctly monitor the inhaling flow trigger of the patient.

If an abnormal condition occurs, a deviation may go beyond the safe threshold value. In that case, the processor may firstly judge whether the two sensors 3, 11 still operate normally, for example by comparing their measured values. If these two values are substantially equal, it indicates the control parameter(s) of the inhalation valve 2 deviate(s), and that changes take place to the characteristic curve of the inhalation valve 2. In this case, the microprocessor can adjust the opening of the inhalation valve 2 with reference to the measured value of the patient end flow sensor 11 and then sends a feedback information to inform the user of a drift in the inhalation valve 2 and a necessary calibration. If the deviations of the measured values of the two sensors exceed the corresponding safe threshold values, it needs to find out which sensor still works normally at that moment. This can be done by comparing the control flow value of the inhalation valve 2 firstly with the measured value of the patient end flow sensor 11 and then with the measured value of the ventilator end flow sensor 3, and the sensor whose deviation of the measured flow value is within the safe threshold value can be judged as normal, the microprocessor can carry out a closed-loop flow control taking the measured value of that sensor as the reference value, and at the same time prompts the user to calibrate or remove the faulty sensor.

If the above comparison shows that the deviations between the flow values of the three devices all exceed the corresponding safety threshold value, it indicates that high deviations occur in at least two devices. Because of the dual flow monitoring mode adopted in the present invention, the probability in such occurrences are minimized as compared with the existing products, so this situation rarely occurs. If it needs to continue using this apparatus, it is necessary to judge whether the valves still work normally through self-testing. If normal, the microprocessor then turns into the open-loop flow control mode, i.e. it suspends the flow feedback during the ventilation controlling and continues the operation according to the characteristic curve of the inhalation valve only, and at the same time gives an alarm to remind the user that the valves and sensors need to be calibrated; if abnormal, the microprocessor has no choice but to shut down the apparatus and gives an alarm at the same time.

In another embodiment according to the present invention, it is possible to simplify the said two-way ventilator end flow sensor 3 to a one-way flow sensor which only measures the inlet gas installed in the drive gas conduits (not limited to the location as illustrated in FIG. 2). Consequently, by only comparing the control parameters with the values of the gas flow measured during the same inhaling gas control period and adjusting the system, it is still possible to send a warning to the user when a failure occurs in the patient end flow sensor 11, reminding the user to take proper measures, thus greatly improving the safety of the mechanical ventilation.

The method according to the present invention has been tested and verified feasible in anesthetic machines, and besides the apparatus achieves more accurate monitored results and has higher safety.

The present invention has been described above by way of the specific embodiments, which are illustrative only and not intended to limit the present invention. Those skilled in the art will appreciate that various combinations of the steps of the method and modifications to the apparatus are possible in light of the teaching of the present invention. Therefore, the scope of protection of the present invention should be defined by the appended claims.

The invention claimed is:

1. An apparatus for monitoring and controlling flows in medical equipment including an anesthetic machine and a ventilator for influencing a patient's respiratory system, said apparatus comprising:
    a power supply,
    a microprocessor,
    an airway system,
    a plurality of microprocessor-controlled valve state monitoring units and valve actuating units, and
    a plurality of sensor data collecting and receiving units;
        said airway system comprising:
            a bellows and drive gas conduits at a ventilator end and breathing tubing at a patient end connected respectively to an outer chamber and a gasbag of the bellows;
            said drive gas conduits connecting:
                a pressure-reducing valve,
                an inhalation valve comprising an adjustable opening controlled by the microprocessor to select a control flow speed through the drive gas conduits during an inhalation period, and
                an exhalation valve for gas-discharging;
            said breathing tubing at the patient end comprising:
                an inhaling conduit, and
                an exhaling conduit;
            said inhalation valve being connected to the corresponding valve state monitoring units and valve actuating units;

said apparatus further comprising:
- a ventilator end flow sensor provided in the drive gas conduits, and
- a patient end flow sensor in the breathing tubing at the patient end such that the airway system provides a gas flow through a series connection of the inhalation valve, the ventilator end flow sensor, and the patient end flow sensor,
- wherein output signals of the ventilator end flow sensor and the patient end flow sensor are delivered to the respective sensor data collecting and receiving units,
- wherein the microprocessor monitors control parameters of the inhalation valve,
- wherein the microprocessor determines deviations between gas flow values corresponding to the control parameters of the inhalation valve and the output signals of the ventilator end flow sensor and the patient end flow sensor, and
- wherein the microprocessor determines which of the inhalation valve, the ventilator end flow sensor, and the patient end flow sensor operates in an abnormal condition that results in the deviations.

2. The apparatus for monitoring and controlling flows according to claim 1, wherein said patient end flow sensor for measuring flows of inhaled and exhaled gases of the patient comprises either a two-way flow sensor installed following a Y-type connector connecting the patient end breathing tubing to the patient, or two one-way flow sensors respectively installed in the inhaling conduit and the exhaling conduit.

3. The apparatus for monitoring and controlling flows according to claim 1, wherein said ventilator end flow sensor comprises a two-way flow sensor installed in the drive gas conduit between the inhalation valve and the bellows.

4. The apparatus for monitoring and controlling flows according to claim 1, wherein said ventilator end flow sensor comprises a one-way flow sensor for measuring the introduced drive gas flow and for calibrating the patient end flow sensor or the inhalation valve, said ventilator end flow sensor being connected between the inhalation valve and a junction where conduits of the exhalation valve and the inhalation valve are connected to each other.

5. A method for monitoring and controlling flows adapted for use in medical equipment including an anesthetic machine and a ventilator for influencing a patient's respiratory system, said equipment comprising a microprocessor, an airway system, a plurality of microprocessor-controlled valve state monitoring units and valve actuating units, and a plurality of sensor data collecting and receiving units, said airway system comprising drive gas conduits connecting an inhalation valve, an exhalation valve for gas-discharging, and an equipment end flow sensor for measuring the drive gas flow introduced or discharged through the inhalation valve and the exhalation valve; said airway system further comprising a patient end breathing tubing which is provided with a patient end flow sensor for measuring flows of inspired and expired gases of the patient; said method comprising the following steps:

(A) the microprocessor actuates the airway system into an inhaling control period and an exhaling control period alternately through the valve actuating units, wherein the microprocessor controls the inhalation valve to select a control flow speed through the airway system during the inhaling period;

(B) the microprocessor monitors control parameters of the inhalation valve through the valve state monitoring units;

(C) the microprocessor acquires gas flow values monitored and measured by the equipment end flow sensor and the patient end flow sensor through the sensor data collecting and receiving units, wherein the acquired gas flow values correspond to a gas flowing through a series connection of the inhalation valve, the ventilator end flow sensor, and the patient end flow sensor; and (D) the microprocessor analyzes and compares the control parameters with the respective gas flow values measured during a same inhaling control period or during a same exhaling control period, carries out adjustment based on the analyzed and compared result, determines deviations between the control parameters and the respective measured gas flow values, and determines which of the inhalation valve, the ventilator end flow sensor, and the patient end flow sensor operates in an abnormal condition that results in the deviations.

6. The method for monitoring and controlling flows according to claim 5, wherein said control parameters include the gas flow actually delivered through the inhalation valve during the inhaling control period, which is the integration of the gas delivering velocity and the gas delivering time through the inhalation valve.

7. The method for monitoring and controlling flows according to claim 5, wherein corresponding safety threshold values are determined for the deviations between the control parameters and the respective measured gas flow values, and for deviations between the respective measured gas flow values themselves, according to fresh gas flow values and an allowable range of error in the measurement of the respective sensors, said safety threshold values being applied to the analysis and comparison in step D.

8. The method for monitoring and controlling flows according to claim 6, wherein corresponding safety threshold values are determined for the deviations between the control parameters and the respective measured gas flow values, and for deviations between the respective measured gas flow values themselves, said safety threshold values being applied to the analysis and comparison in step D.

9. The method for monitoring and controlling flows according to claim 7, wherein, in step D, the microprocessor carries out a closed-loop flow control taking the measured value of the patient end flow sensor as a reference value, when it judges that the deviations between the control flow of the inhalation valve, the measured flow of the equipment end flow sensor, and the measured flow of the patient end flow sensor are within the respective safety threshold values.

10. The method for monitoring and controlling flows according to claim 7, wherein, in step D, the microprocessor carries out a closed-loop flow control taking the measured value of the patient end flow sensor as the reference value and prompts the user that the inhalation valve needs to be calibrated, when it judges that the measured value of the equipment end flow sensor and the measured value of the patient end flow sensor are substantially equal, while the deviations between the control parameters and these measured values exceed the corresponding safe threshold values.

11. The method for monitoring and controlling flows according to claim 7, wherein, in step D, upon judging that the deviations between the measured flow of the equipment end flow sensor and the measured flow of the patient end flow sensor exceed the corresponding safety threshold values, the microprocessor compares firstly the control parameters of the inhalation valve with the measured value of the patient end flow sensor and, if the deviations are within the corresponding safety threshold values, carries out a closed-loop flow control taking the measured value of the patient end flow sensor as the reference value; otherwise the microprocessor compares then the control parameters with the measured value of the equipment end flow sensor and, if the deviations are within the corresponding safety threshold values, carries out a closed-loop flow control taking the measured value of the equipment end flow sensor as the reference value.

12. An apparatus for monitoring and controlling flows adapted for use in medical equipment for influencing a patient's respiratory system, especially in an anesthetic machine and a ventilator, said apparatus comprising:

an airway system, which comprises an inhalation valve and an exhalation valve installed in drive gas conduits, an equipment end flow sensor for measuring at least one of the introduced and discharged drive gas flow through at least one of the inhalation valve and the exhalation valve, and a patient end flow sensor for measuring the patient's inspired and expired gas flow, wherein the airway system provides a series connection of the equipment end flow sensor and the patient end flow sensor, wherein the inhalation valve comprises an adjustable opening controlled by the microprocessor to select among a plurality of possible control flow speeds through the drive gas conduits during an inhalation period, valve state monitoring units and valve actuating units connected to at least one of the inhalation valve and the exhalation valve, sensor data collecting and receiving units associated with the equipment end flow sensor and the patient end flow sensor, a microprocessor for controlling the valve state monitoring units, the valve actuating units and the sensor data collecting and receiving units, wherein the microprocessor is configured to analyze and compare the measured flow values of the equipment end flow sensor and the patient end flow sensor and with control parameters of at least one of the inhalation valve and the exhalation valve and thereby is configured to determine and control the operation states of the respective flow sensors and valves so as to control the flows accurately, wherein the microprocessor determines deviations between gas flow values corresponding to the control parameters of the inhalation valve and the output signals of the ventilator end flow sensor and the patient end flow sensor, and wherein the microprocessor determines which of the inhalation valve, the ventilator end flow sensor, and the patient end flow sensor operates in an abnormal condition that results in the deviations.

* * * * *